United States Patent [19] [11] 4,324,553
Bugaut et al. [45] Apr. 13, 1982

[54] HAIR DYEING COMPOSITIONS CONTAINING AT LEAST ONE 2,4-DIAMINO-ALKYLBENZENE AS COUPLER

[75] Inventors: Andrée Bugaut, Boulogne; Alex Junino, Aulnay Sous Bois, both of France

[73] Assignee: L'Oreal, Paris, France

[21] Appl. No.: 166,234

[22] Filed: Jul. 7, 1980

[30] Foreign Application Priority Data

Jul. 24, 1979 [FR] France ................................. 79 19039

[51] Int. Cl.$^3$ .............................................. A61K 7/13

[52] U.S. Cl. ............................................ 8/407; 8/406; 8/408; 8/409; 8/411; 8/412; 8/414; 8/421; 8/423; 8/424

[58] Field of Search .................. 8/411, 407, 416, 406, 8/408, 409, 412, 414, 421–424

[56] References Cited

U.S. PATENT DOCUMENTS 1,144,325  6/1915  Erlenbach ............................... 8/411
4,092,102  5/1978  Halasz et al. .......................... 8/411
4,171,203  10/1979  Rose et al. ............................. 8/416

*Primary Examiner*—Donald B. Moyer

[57] ABSTRACT

The invention provides as a coupling component for an oxidation hair dye composition a meta-diaminoalkylbenzene or a salt thereof, the alkyl substituent being n-propyl, iso-propyl or n-butyl.

34 Claims, No Drawings

HAIR DYEING COMPOSITIONS CONTAINING AT LEAST ONE 2,4-DIAMINO-ALKYLBENZENE AS COUPLER

DESCRIPTION

This invention relates to hair dyeing compositions containing an oxidation base and a coupler.

The importance of meta-phenylenediamines as couplers in so-called oxidation hair dyeing is well known. In fact, these couplers have a dual importance by making it possible to provide two fundamental shades in the formulation of hair-dyeing compositions. In association with para-phenylenediamines, in an oxidising alkaline medium, typically an ammoniacal medium in the presence of hydrogen peroxide, they lead to indamines which impart, to the hair, colorations ranging from blue-greens to purple-blues. Furthermore, in association with para-aminophenols, they lead, by means of oxidative coupling, to indoanilines which impart, to the hair, colorations ranging from oranges to purples.

An addition to the class of the meta-phenylene-diamines known for hair dyeing is particularly advantageous if the basic necessity for preparing harmless dyes is combined with the idea of preparing dyes having good qualities from the aesthetic point of view. In fact, 2,4-diaminotoluene, which has been used in hair dyeing for a long time, is now prohibited because of its toxicity; in particular, this product possesses a very high mutagenic activity as evaluated in the Ames test on Salmonella typhimurium (TA 1538 and TA 98), in the presence of "S9 mix" induced by "Aroclor 1254" (see for example, Ames "The detection of chemical mutagens with enteric bacteria in a Hollander", Chemical Mutagens, Principles and Methods for their detection, Vol. 1, Plenum Press, New York, 1971, pp 267–282 and Ames, McCann and Yamasaki, "Methods of detecting carcinogens and mutagens with the Salmonella/mammalian microsome mutagenicity test", Mutation Research, 31, 1975 pp 347–364.). 2,4-Diamino-ethylbenzene also possesses a high mutagenic activity.

In contrast, it has surprisingly been found, according to the invention, that the compounds of the formula (I)

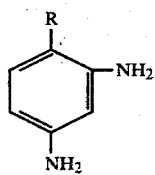

in which formula R represents a n-propyl, isopropyl or n-butyl radical, and also their salts, such as the hydrochloride, sulphate, citrate and lactate, have dyeing qualitites equivalent to those of 2,4-diaminotoluene and lead to dyes having excellent stability to shampoos, but are also devoid of activity in the Ames test under the conditions specified above. The compounds of formula (I) are known as chemical compounds but, so far as we are aware, they have never been proposed for use in hair-dyeing compositions.

The present invention consequently provides a hair-dyeing composition containing at least one oxidation base in a cosmetic carrier, characterized in that it contains at least one meta-phenylenediamine of the formula (I), or one of its salts, as the coupler.

In general terms, the meta-phenylenediamines of the formula (I) are present in the dyeing composition according to the invention in an amount of 0.005 to 2.5% by weight, relative to the total weight of the composition.

The following may be mentioned among the oxidation bases which can advantageously be used in the dyeing compositions according to the invention:

(a) para-phenylenediamines, in particular paraphenylenediamine, para-toluylenediamine, 2,6-dimethylparaphenylenediamine, 2,3-dimethyl-para-phenylenediamine, N-(β-methoxyethyl)-para-phenylenediamine, N,N-di-(β-hydroxyethyl)-para-phenylenediamine, N-ethyl-N-(β-hydroxyethyl)-para-phenylenediamine, 2,6-dimethyl-3-methoxypara-phenylenediamine, N-ethyl-N-(β-mesylaminoethyl)-para-phenylenediamine, N-ethyl-N-carbamylmethyl-para-phenylenediamine, 2,5-diamino-isopropylbenzene and 2,5-diaminophenylethanol;

(b) 2,5-diaminopyridine; and (c) para-aminophenols, for example para-aminophenol, 2-methyl-4-aminophenol, 2,6-dimethyl-4-aminophenol and 2-chloro-4-aminophenol.

The compositions according to the invention can contain couplers other than the compounds of the formula (I), in particular resorcinol, 2-methylresorcinol, meta-aminophenol, 2-methyl-5-N-(β-hydroxyethyl)-aminophenol, 2-methyl-5-aminophenol, 6-hydroxybenzomorpholine, 2-methyl-5-N-(carbamylmethyl)-aminophenol or 2,6-dimethyl-5-acetylaminophenol, or couplers with an active methylene group, such as 1-phenyl-3-methylpyrazol-5-one, or also other meta-phenylenediamines, such as 2,4-diaminophenoxyethanol. They can also contain α-naphthol.

The dyeing compositions according to the invention can also contain compounds which, via complex oxidation mechanisms, can react either with themselves or with para-phenylenediamines; ortho-aminophenol, pyrocatechol and hydroquinone may be mentioned, in particular, among such compounds. The compositions can also contain benzene dyestuff precursors, the nucleus of which carries at least three substituents chosen from hydroxyl, methoxy and amino groups, such as 1,2,4-trihydroxybenzene, or precursors of the naphthalene series, such as 2-hydroxy-1,4-naphthoquinone or 5-hydroxy-1,4-naphthoquinone.

The compositions according to the invention can also contain direct dyestuffs for enriching the dye with various sheens. Nitrobenzene derivatives, such as 3-nitro-6-N-(β-hydroxyethyl)-aminoanisole, 3-nitro-4-aminophenol, 3-nitro-4-N-(β-hydroxyethyl)-aminophenol, 4-nitro-5-N-methylaminophenoxyethanol, 2-amino-3-nitroisopropylbenzene, 3-nitro-4-N-methylamino-N,N-di-(β-hydroxyethyl)-aniline, 2-amino-3-nitrophenol, 2-nitro-4-methyl-6-aminophenol and 2-methyl-4-amino-5-nitrophenol, can be used in particular.

The dyeing compositions according to the invention can also contain various customary adjuvants, such as penetrating agents, foaming agents, thickeners, anti-oxidants, alkalizing or acidifying agents, perfumes, sequestering agents, film-forming products and organic solvents.

The pH of the dyeing compositions according to the invention is basic, for example from 8 to 11.5. Suitable alkalizing agents which can be used to provide this pH include ammonia, alkylamines, such as ethylamine or triethylamine, alkanolamines, such as mono-, di or triethanolamine, alkylalkanolamines, such as methyldiethanolamine, sodium hydroxide or potassium hydroxide, sodium carbonate, potassium carbonate or ammonium carbonate. Among the acidifying agents which can be used, there may be mentioned lactic acid, acetic acid, tartaric acid and phosphoric acid.

Anionic, cationic, non-ionic or amphoteric water-soluble surface-active agents can also be included in the compositions according to the invention. Amongst the surface-active agents which can be used in particular, there may be mentioned alkylbenzenesulphonates, alkyl-naphthalenesulphonates, sulphates, ether-sulphates and sulphonates of fatty alcohols, quaternary ammonium salts, such as trimethylcetylammonium bromide and cetyl-pyridinium bromide, diethanolamides of fatty acids, polyoxyethyleneated or polyglycerolated acids and alcohols and polyoxyethyleneated or polyglycerolated alkylphenols. Preferably, the surface-active agents are present in the compositions according to the invention in a proportion of 0.5 to 55% by weight, and advantageously 4 to 40% by weight, relative to the total weight of the composition.

Organic solvents can also be included in the compositions according to the invention in order to solubilize compounds which otherwise would not be sufficiently soluble in water. Among the solvents which can advantageously be used, there may be mentioned ethanol, isopropanol, glycerol, glycols and their ethers, such as 2-butoxyethanol, ethylene glycol, propylene glycol and diethylene glycol monoethyl ether and monomethyl ether, and analogous solvents. The solvents are advantageously present in the compositions in a proportion from 1 to 40% by weight, and preferably from 5 to 30% by weight, relative to the total weight of the composition.

The thickeners which can be included in the compositions according to the invention are advantageously sodium alginate, gum arabic, cellulose derivatives, such as methylcellulose, hydroxyethyl-cellulose, hydroxypropylmethylcellulose and the sodium salt of carboxymethylcellulose, and acrylic acid polymers; inorganic thickeners, such as bentonite, can also be used. Preferably, the thickeners are present in a proportion of 0.5 to 5% by weight, and advantageously 0.5 to 3% by weight, relative to the total weight of the composition.

The antioxidants which can be included in the compositions according to the invention are advantageously sodium sulphite, thioglycolic acid, sodium bisulphite, ascorbic acid or hydroquinone. These antioxidants are suitably present in an amount from 0.05 to 1.5% by weight, relative to the total weight of the composition.

At the time of use, the dyeing compositions according to the invention contain oxidizing agents, such as hydrogen peroxide, urea peroxide or per-salts, such as ammonium persulphate.

The dyeing composition according to the invention is suitably in the form of a liquid, cream, gel or aerosol or in any other form suitable for dyeing keratin fibres.

The present invention also provides a process for coloring the hair, which comprises mixing the composition of the invention, containing at least one compound of the formula (I), at the time of use with a sufficient amount of an oxidizing agent, applying the said mixture to the hair for, say, 10 to 45 minutes and at a temperature ranging from ambient temperature to 45° C., and then rinsing the hair, optionally washing and rinsing it again, and drying it.

The following Examples further illustrate the present invention.

EXAMPLE 1

The following dyeing composition is prepared:

| | | |
|---|---|---|
| 2,4-Diamino-n-butylbenzene dihydrochloride | 0.1 | g |
| 2-Methyl-5-N-(β-hydroxyethyl)-aminophenol | 0.20 | g |
| 2,6-Dimethyl-para-phenylenediamine dihydrochloride | 0.3 | g |
| Para-phenylenediamine | 0.05 | g |
| 3-Nitro-4-N-methylamino-N,N-di-(β-hydroxyethyl)-aniline | 0.7 | g |
| Oxyethyleneated oleyl alcohol containing two mols of ethylene oxide (per mol of alcohol) | 4.5 | g |
| Oxyethyleneated oleyl alcohol containing four mols of ethylene oxide | 4.5 | g |
| Oxyethyleneated oleylamine containing twelve mols of ethylene oxide, sold by "ARMOUR" under the name "ETHOMEEN T012" | 4.5 | g |
| Diethanolamides of copra fatty acids | 9 | g |
| Propylene glycol | 4 | g |
| 2-Butoxyethanol | 8 | g |
| Ethanol (96° strength) | 6 | g |
| The pentasodium salt of diethylenetriaminepentaacetic acid | 2 | g |
| Thioglycolic acid | 0.5 | g |
| Ammonia solution (22° B strength) | 4 | g |
| Water q.s.p. | 100 | g |

The pH of the composition is equal to 9.6.

100 g of hydrogen peroxide of 20 volumes strength are added at the time of use.

When applied to 90% naturally white hair for 25 minutes at 27° C., this mixture imparts to the hair, after rinsing and shampooing, a silvery mauve-grey coloration.

EXAMPLE 2

The following dyeing composition is prepared:

| | | |
|---|---|---|
| 2,4-Diamino-n-propylbenzene dihydrochloride | 0.125 | g |
| 2,5-Diaminopyridine dihydrochloride | 0.54 | g |
| Para-phenylenediamine | 0.04 | g |
| Pyrocatechol | 0.4 | g |
| 2-Methyl-5-N-(β-hydroxyethyl)-aminophenol | 0.125 | g |
| 2-Amino-3-nitro-isopropylbenzene | 0.03 | g |
| Oxyethyleneated oleyl alcohol containing two mols of ethylene oxide | 4.5 | g |
| Oxyethyleneated oleyl alcohol containing four mols of ethylene oxide | 4.5 | g |
| Oxyethyleneated oleylamine containing twelve mols of ethylene oxide, sold by "ARMOUR" under the name "ETHOMEEN T012" | 4.5 | g |
| Diethanolamides of copra fatty acids | 9 | g |
| Propylene glycol | 4 | g |
| 2-Butoxyethanol | 8 | g |
| Ethanol (96° strength) | 6 | g |
| The pentasodium salt of diethylenetriaminepentaacetic acid | 2 | g |
| Hydroquinone | 0.15 | g |
| Sodium bisulphite (35° B strength aqueous solution) | 1.3 | g |
| Ammonia solution (22° B strength) | 2.4 | g |
| Water q.s.p. | 100 | g |

The pH of the composition is equal to 9.4.

60 g of hydrogen peroxide of 20 volumes strength are added at the time of use.

When applied to bleached hair for 20 minutes at 27° C., this mixture imparts to the hair, after rinsing and shampooing, a pearlescent ashen beige coloration.

EXAMPLE 3

The following dyeing composition is prepared:

| | | |
|---|---|---|
| 2,4-Diamino-isopropylbenzene dihydrochloride | 0.15 | g |
| 2-Methyl-5-N-(β-hydroxyethyl)-aminophenol | 0.1 | g |
| 2-Methylresorcinol | 0.25 | g |
| Meta-aminophenol | 0.25 | g |
| Para-phenylenediamine | 0.23 | g |
| Para-aminophenol | 0.6 | g |
| Ortho-aminophenol | 0.27 | g |
| Oxyethyleneated oleyl alcohol containing two mols of ethylene oxide | 4.5 | g |
| Oxyethyleneated oleyl alcohol containing four mols of ethylene oxide | 4.5 | g |
| Oxyethyleneated oleylamine containing twelve mols of ethylene oxide, sold by "ARMOUR" under the name "ETHOMEEN T012" | 4.5 | g |
| Diethanolamides of copra fatty acids | 9 | g |
| Propylene glycol | 4 | g |
| 2-Butoxyethanol | 8 | g |
| Ethanol (96° strength) | 6 | g |
| The pentasodium salt of diethylenetriamine-pentaacetic acid | 2 | g |
| Hydroquinone | 0.15 | g |
| Sodium bisulphite (35° B strength aqueous solution) | 1.3 | g |
| Triethanolamine | 1.2 | g |
| Water q.s.p. | 100 | g |

The pH of the composition is equal to 8.6.

100 g of hydrogen peroxide of 20 volumes strength are added at the time of use.

When applied to 90% naturally white hair for 25 minutes at 30° C., this mixture imparts to the hair, after rinsing and shampooing, a medium chestnut coloration.

EXAMPLE 4

The following dyeing composition is prepared:

| | | |
|---|---|---|
| 2,4-Diamino-n-butylbenzene dihydrochloride | 2.4 | g |
| Para-phenylenediamine | 2.4 | g |
| Ortho-aminophenol | 1.60 | g |
| Sodium lauryl-sulphate containing two mols of ethylene oxide | 19 | g |
| Ethylenediaminetetraacetic acid | 0.19 | g |
| 2-Butoxyethanol | 3.8 | g |
| Sodium bisulphite (35° B strength aqueous solution) | 0.9 | g |
| Hydroquinone | 0.14 | g |
| Ammonia solution (22° B strength) | 10 | g |
| Water q.s.p. | 100 | g |

The pH of the composition is equal to 9.9.

100 g of hydrogen peroxide of 20 volumes strength are added at the time of use.

When applied for 25 minutes at 25° C. to hair which has been bleached white, this mixture imparts to the hair, after rinsing and shampooing, a blue-black coloration.

EXAMPLE 5

The following dyeing composition is prepared:

| | | |
|---|---|---|
| 2,4-Diamino-n-propylbenzene dihydrochloride | 0.156 | g |
| 2-Methyl-5-N-(β-hydroxyethyl)-aminophenol | 0.25 | g |
| Meta-aminophenol | 0.109 | g |
| Resorcinol | 0.11 | g |
| N-(β-Methoxyethyl)-para-phenylenediamine dihydrochloride | 0.72 | g |
| 3-Nitro-4-aminophenol | 0.2 | g |
| 3-Nitro-4-N-(β-hydroxyethyl)-aminophenol | 0.1 | g |
| Crosslinked polyacrylic acid sold under the name "CARBOPOL 934" | 1.5 | g |
| Ethanol (96° strength) | 11 | g |
| 2-Butoxyethanol | 5 | g |
| Trimethylcetylammonium bromide | 1 | g |
| Ethylenediaminetetraacetic acid | 0.1 | g |
| Ammonia solution (22° B strength) | 10 | g |
| Thioglycolic acid | 0.2 | g |
| Water q.s.p. | 100 | g |

The pH of the composition is equal to 10.1.

100 g of hydrogen peroxide of 20 volumes strength are added at the time of use.

When applied to 90% naturally white hair for 30 minutes at 27° C., this mixture imparts to the hair, after rinsing and shampooing, a medium chestnut coloration with a slight coppery sheen.

EXAMPLE 6

The following dyeing composition is prepared:

| | | |
|---|---|---|
| 2,4-Diamino-isopropylbenzene dihydrochloride | 0.2 | g |
| 2-Methyl-5-aminophenol | 0.2 | g |
| 2,6-Dimethyl-para-phenylenediamine dihydrochloride | 0.2 | g |
| 4-Amino-N-(β-methoxyethyl)-aniline dihydrochloride | 0.3 | g |
| 2-Methyl-4-amino-5-nitrophenol | 0.08 | g |
| 3-Nitro-4-N-(β-hydroxyethyl)-aminophenol | 0.04 | g |
| Nonylphenol containing four mols of ethylene oxide, sold by "RHONE POULENC" under the name "CEMULSOL NP4" | 21 | g |
| Nonylphenol containing nine mols of ethylene oxide, sold by "RHONE POULENC" under the name "CEMULSOL NP9" | 24 | g |
| Oleic acid | 4 | g |
| 2-Butoxyethanol | 3 | g |
| Ethanol (96° strength) | 10 | g |
| The pentasodium salt of diethylenetriamine-pentaacetic acid | 2.5 | g |
| Thioglycolic acid | 0.6 | g |
| Ammonia solution (22° B strength) | 10 | g |
| Water q.s.p. | 100 | g |

The pH of the composition is equal to 10.

100 g of hydrogen peroxide of 20 volumes strength are added at the time of use.

When applied to 90% naturally white hair for 30 minutes at 27° C., this mixture imparts to the hair, after rinsing and shampooing, a bluish silver-grey coloration.

EXAMPLE 7

The following dyeing composition is prepared:

| | | |
|---|---|---|
| 2,4-Diamino-isopropylbenzene dihydrochloride | 0.005 | g |
| 2-Methyl-5-N-(β-hydroxyethyl)-aminophenol | 0.0175 | g |
| Resorcinol | 0.01 | g |
| N-(β-Methoxyethyl)-para-phenylenediamine dihydrochloride | 0.048 | g |
| Sodium lauryl-sulphate containing two mols of ethylene oxide | 20 | g |
| Ethylenediaminetetraacetic acid | 0.2 | g |
| Sodium bisulphite (35° B strength aqueous solution) | 1 | g |
| Ammonia solution (22° B strength) | 10 | g |
| Water q.s.p. | 100 | g |

The pH of the composition is equal to 10.9.

50 g of hydrogen peroxide of 20 volumes strength are added at the time of use.

When applied for 30 minutes at 25° C. to hair which has been bleached white, this mixture imparts to the hair, after rinsing and shampooing, a pearlescent very light blond coloration.

EXAMPLE 8

The following dyeing composition is prepared:

| | | |
|---|---|---|
| 2,4-Diamino-n-butylbenzene dihydrochloride | 0.16 | g |
| Resorcinol | 0.4 | g |
| Meta-aminophenol | 0.23 | g |
| 2-Methyl-5-aminophenol | 0.3 | g |
| Para-aminophenol | 0.5 | g |
| Para-toluylenediamine dihydrochloride | 0.75 | g |
| Ortho-nitroaniline | 0.03 | g |
| Nonylphenol containing four mols of ethylene oxide, sold by "RHONE POULENC" under the name "CEMULSOL NP4" | 21 | g |
| Nonylphenol containing nine mols of ethylene oxide, sold by "RHONE POULENC" under the name "CEMULSOL NP9" | 24 | g |
| Oleic acid | 4 | g |
| 2-Butoxyethanol | 3 | g |
| Ethanol (96° strength) | 10 | g |
| The pentasodium salt of diethylenetriaminepentaacetic acid | 2.5 | g |
| Thioglycolic acid | 0.6 | g |
| Ammonia solution (22° B strength) | 10 | g |
| Water q.s.p. | 100 | g |

The pH of the composition is equal to 9.9.

100 g of hydrogen peroxide of 20 volumes strength are added at the time of use.

When applied for 30 minutes at 28° C. to hair which has been bleached white, this mixture imparts to the hair, after rinsing and shampooing, a mahogany coloration.

EXAMPLE 9

The following dyeing composition is prepared:

| | | |
|---|---|---|
| 2,4-Diamino-n-propylbenzene dihydrochloride | 0.15 | g |
| Meta-aminophenol | 0.25 | g |
| 6-Hydroxybenzomorpholine | 0.07 | g |
| 2,6-Dimethyl-3-methoxy-para-phenylenediamine dihydrochloride | 0.08 | g |
| N,N-di-(β-Hydroxyethyl)-para-phenylenediamine dihydrochloride | 0.18 | g |
| Para-aminophenol | 0.15 | g |
| 4-N-Methylaminophenol | 0.15 | g |
| 3-Nitro-4-N-(β-hydroxyethyl)-aminophenol | 0.3 | g |
| Sodium lauryl-sulphate containing two mols of ethylene oxide | 20 | g |
| Ethylenediaminetetraacetic acid | 0.2 | g |
| Sodium bisulphite (35° B strength aqueous solution) | 1 | g |
| Hydroquinone | 0.15 | g |
| Ammonia solution (22° B strength) | 10 | g |
| Water q.s.p. | 100 | g |

The pH of the composition is equal to 10.8.

80 g of hydrogen peroxide of 20 volumes strength are added at the time of use.

When applied to 90% naturally white hair for 30 minutes at 27° C., this mixture imparts to the hair, after rinsing and shampooing, a pinkish light chestnut coloration with a golden sheen.

EXAMPLE 10

The following dyeing composition is prepared:

| | | |
|---|---|---|
| 2,4-Diamino-isopropylbenzene dihydrochloride | 1 | g |
| 2,5-Diaminopyridine dihydrochloride | 1.5 | g |
| Pyrocatechol | 0.327 | g |
| Resorcinol | 0.11 | g |
| 1-Phenyl-3-methylpyrazol-5-one | 0.087 | g |
| 2-Nitro-4-methyl-6-aminobenzene | 0.7 | g |
| Sodium lauryl-sulphate containing two mols of ethylene oxide | 20 | g |
| Ethylenediaminetetraacetic acid | 0.2 | g |
| Sodium bisulphite (35° B strength aqueous solution) | 1 | g |
| Hydroquinone | 0.15 | g |
| Ammonia solution (22° B strength) | 10 | g |
| Water q.s.p. | 100 | g |

The pH of the composition is equal to 9.9.

100 g of hydrogen peroxide of 20 volumes strength are added at the time of use.

When applied for 25 minutes at 27° C. to hair which has been bleached straw yellow, this mixture imparts to the hair, after rinsing and shampooing, a copper-red chestnut coloration.

EXAMPLE 11

The following dyeing composition is prepared:

| | | |
|---|---|---|
| 2,4-Diamino-n-propylbenzene dihydrochloride | 1.12 | g |
| Para-phenylenediamine | 0.54 | g |
| Sodium lauryl-sulphate containing two mols of ethylene oxide | 20 | g |
| Ethylenediaminetetraacetic acid | 0.2 | g |
| Sodium bisulphite (35° B strength aqueous solution) | 1 | g |
| Hydroquinone | 1.5 | g |
| Ammonia solution (22° B strength) | 10 | g |
| Water q.s.p. | 100 | g |

The pH of the composition is equal to 10.3.

100 g of hydrogen peroxide of 20 volumes strength are added at the time of use.

When applied for 20 minutes at 28° C. to hair which has been bleached white, this mixture imparts to the hair, after rinsing and shampooing, an intense purple-blue coloration.

EXAMPLE 12

The following dyeing composition is prepared:

| | | |
|---|---|---|
| 2,4-Diamino-n-butylbenzene dihydrochloride | 2.5 | g |
| Para-phenylenediamine | 1.8 | g |
| Crosslinked polyacrylic acid sold under the name "CARBOPOL 934" | 1.5 | g |
| Ethanol (96° strength) | 11 | g |
| 2-Butoxyethanol | 5 | g |
| Trimethylcetylammonium bromide | 1 | g |
| Ethylenediaminetetraacetic acid | 0.1 | g |
| Ammonia solution (22° B strength) | 10 | g |
| Thioglycolic acid | 0.2 | g |
| Water q.s.p. | 100 | g |

The pH of the composition is equal to 9.8.

100 g of hydrogen peroxide of 20 volumes strength are added at the time of use.

When applied to 90% naturally white hair for 20 minutes at 25° C., this mixture imparts to the hair, after rinsing and shampooing, a dark blue coloration shaded with purple.

EXAMPLE 13

The following dyeing composition is prepared:

| | | |
|---|---|---|
| 2,4-Diamino-n-propylbenzene dihydrochloride | 0.25 | g |
| 2-Methyl-5-N-(β-hydroxyethyl)-aminophenol | 0.6 | g |
| Para-phenylenediamine | 0.5 | g |
| 3-Nitro-4-N-(β-hydroxyethyl)-aminophenol | 0.5 | g |

-continued

| | | |
|---|---|---|
| 3-Nitro-6-N-(β-hydroxyethyl)-aminoanisole | 0.5 | g |
| 3-Nitro-4-aminophenol | 1.5 | g |
| Oxyethyleneated oleyl alcohol containing two mols of ethylene oxide | 4.5 | g |
| Oxyethyleneated oleyl alcohol containing four mols of ethylene oxide | 4.5 | g |
| Oxyethyleneated oleylamine containing twelve mols of ethylene oxide, sold by "ARMOUR" under the name "ETHOMEEN T012" | 4.5 | g |
| Diethanolamides of copra fatty acids | 9 | g |
| Propylene glycol | 4 | g |
| 2-Butoxyethanol | 8 | g |
| Ethanol (96° strength) | 6 | g |
| The pentasodium salt of diethylenetriamine-pentaacetic acid | 2 | g |
| Hydroquinone | 0.15 | g |
| Sodium bisulphite (35° B strength aqueous solution) | 1.3 | g |
| Ammonia solution (22° B strength) | 10 | g |
| Water q.s.p. | 100 | g |

The pH of the composition is equal to 10.5.

100 g of hydrogen peroxide of 20 volumes strength are added at the time of use.

When applied to 90% naturally white hair for 25 minutes at 25° C., this mixture imparts to the hair, after rinsing and shampooing, a red coloration.

EXAMPLE 14

The following dyeing composition is prepared:

| | | |
|---|---|---|
| 2,4-Diamino-n-propylbenzene dihydrochloride | 0.892 | g |
| Para-aminophenol | 0.436 | g |
| Sodium lauryl-sulphate containing two mols of ethylene oxide | 20 | g |
| Ethylenediaminetetraacetic acid | 0.2 | g |
| Sodium bisulphite (35° B strength aqueous solution) | 1 | g |
| Hydroquinone | 1.5 | g |
| Ammonia solution (22° B strength) | 10 | g |
| Water q.s.p. | 100 | g |

The pH of the composition is equal to 10.4.

100 g of hydrogen peroxide of 20 volumes strength are added at the time of use.

When applied to 90% naturally white hair for 20 minutes at 28° C., this mixture imparts to the hair, after rinsing and shampooing, a light purple-violet coloration.

EXAMPLE 15

The following dyeing composition is prepared:

| | | |
|---|---|---|
| 2,4-Diamino-isopropylbenzene dihydrochloride | 0.446 | g |
| N-Ethyl-N-(β-hydroxyethyl)-para-phenylene-diamine dihydrochloride | 0.506 | g |
| Sodium lauryl-sulphate containing two mols of ethylene oxide | 20 | g |
| Sodium bisulphite (35° B strength aqueous solution) | 1 | g |
| Ammonia solution (22° B strength) | 10 | g |
| Water q.s.p. | 100 | g |

The pH of the composition is equal to 10.4.

50 g of hydrogen peroxide of 20 volumes strength are added at the time of use.

When applied to 90% naturally white hair for 30 minutes at 28° C., this mixture imparts to the hair, after rinsing and shampooing, a light emerald-blue coloration.

EXAMPLE 16

The following dyeing composition is prepared:

| | | |
|---|---|---|
| 2,4-Diamino-isopropylbenzene dihydrochloride | 0.669 | g |
| 2,5-Diamino-isopropylbenzene dihydrochloride | 0.669 | g |
| Oxyethyleneated oleyl alcohol containing two mols of ethylene oxide | 4.5 | g |
| Oxyethyleneated oleyl alcohol containing four mols of ethylene oxide | 4.5 | g |
| Oxyethyleneated oleylamine containing twelve mols of ethylene oxide, sold by "ARMOUR" under the name "ETHOMEEN T012" | 4.5 | g |
| Diethanolamides of copra fatty acids | 9 | g |
| Propylene glycol | 4 | g |
| 2-Butoxyethanol | 8 | g |
| Ethanol (96° strength) | 6 | g |
| The pentasodium salt of diethylenetriamine-pentaacetic acid | 2 | g |
| Thioglycolic acid | 0.5 | g |
| Ammonia solution (22° B strength) | 10 | g |
| Water q.s.p. | 100 | g |

The pH of the composition is equal to 9.8.

100 g of hydrogen peroxide of 20 volumes strength are added at the time of use.

When applied for 20 minutes at 23° C. to hair which has been bleached white, this mixture imparts to the hair, after rinsing and shampooing, an intense pure blue coloration.

EXAMPLE 17

The following dyeing composition is prepared:

| | | |
|---|---|---|
| 2,4-Diamino-n-butylbenzene | 0.587 | g |
| 2,5-Diaminophenyl-ethanol dihydrochloride | 0.81 | g |
| Sodium lauryl-sulphate containing two mols of ethylene oxide | 20 | g |
| Ethylenediaminetetraacetic acid | 0.2 | g |
| Sodium bisulphite (35° B strength aqueous solution) | 1 | g |
| Ammonia solution (22° B strength) | 10 | g |
| Water q.s.p. | 100 | g |

The pH of the composition is equal to 10.5.

100 g of hydrogen peroxide of 20 volumes strength are added at the time of use.

When applied to 90% naturally white hair for 25 minutes at 30° C., this mixture imparts to the hair, after rinsing and shampooing, a silvery blue coloration.

We claim:

1. A composition suitable for dyeing human hair in the presence of an oxidizing agent selected from the group consisting of hydrogen peroxide, urea peroxide and ammonium persulfate, said composition comprising an aqueous solution of at least one oxidation base and, as a coupler, at least one meta-phenylenediamine of the formula (I)

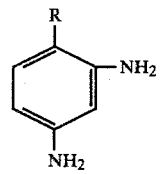

(I)

wherein R represents n-propyl, isopropyl or n-butyl, or a salt thereof.

2. A composition according to claim 1, in which the compound of formula (I), or salt is present in an amount from 0.005 to 2.5% by weight, relative to the total weight of the composition.

3. A composition according to claim 1, in which the oxidation base is selected from the group consisting of:
(a) para-phenylenediamine, para-toluylenediamine, 2,6-dimethyl-para-phenylenediamine, 2,3-dimethyl-para-phenylenediamine, N-(β-methoxyethyl)-para-phenylenediamine, N,N-di-(β-hydroxyethyl)-para-phenylenediamine, N-ethyl-N-(β-hydroxyethyl)-para-phenylenediamine, 2,6-dimethyl-3-methoxy-para-phenylenediamine, N-ethyl-N-(β-mesylaminoethyl)-para-phenylenediamine, N-ethyl-N-carbamylmethyl-para-phenylenediamine, 2,5-diamino-isopropylbenzene and 2,5diaminophenyl-ethanol;
(b) 2,5-diaminopyridine; and
(c) para-aminophenol, 2-methyl-4-aminophenol, 2,6-dimethyl-4-aminophenol and 2-chloro-4-aminophenol.

4. A composition according to claim 1, which contains at least one additional coupler which is selected from the group consisting of resorcinol, 2-methylresorcinol, meta-aminophenol, 2-methyl-5-N-(β-hydroxyethyl)-aminophenol, 2-methyl-5-aminophenol, 6-hydroxybenzomorpholine, 2-methyl-5-N-(carbamylmethyl)-aminophenol and 2,6-dimethyl-5-acetylaminophenol, or 1-phenyl-3-methylpyrazol-5-one or 2,4-diaminophenoxy-ethanol and α-naphthol.

5. A composition according to claim 1, which also contains at least one of ortho-aminophenol, pyrocatechol, 1,2,4-trihydroxybenzene, 2-hydroxy-1,4-naphthoquinone or 5-hydroxy-1,4-naphthoquinone.

6. A composition according to claim 1, which also contains at least one the direct dyestuff selected from the group consisting of 3-nitro-6-N-(β-hydroxyethyl)-aminoanisole, 3-nitro-4-aminophenol, 3-nitro-4-N-(β-hydroxyethyl)-aminophenol, 4-nitro-5-N-methylaminophenoxy-ethanol, 2-amino-3-nitro-isopropylbenzene, 3-nitro-4-N-methylamino-N,N-di-(β-hydroxyethyl)-aniline, 2-amino-3-nitrophenol, 2-nitro-4-methyl-6-aminophenol and 2-methyl-4-amino-5-nitrophenol.

7. A composition according to claim 1, which has a pH of 8 to 11.5.

8. A composition according to claim 1, which also contains at least one alkalizing agent which is ammonia, ethylamine or triethylamine, mono-, di- or tri-ethanolamine, methyldiethanolamine, sodium hydroxide or potassium hydroxide or sodium carbonate, potassium carbonate or ammonium carbonate.

9. A composition according to claim 1, which also contains at least one acidifying agent which is lactic acid, acetic acid, tartaric acid or phosphoric acid.

10. A composition according to claim 1, which contains 0.5 to 55% by weight of surface-active agent, relative to the total weight of the composition.

11. A composition according to claim 10, which contains 4 to 40% by weight of surface-active agent, relative to the total weight of the composition.

12. A composition according to claim 1, which contains at least one organic solvent which is ethanol, isopropanol, glycerol, 2-butoxyethanol, ethylene glycol, propylene glycol or diethylene glycol monoethyl ether or diethylene glycol monomethyl ether.

13. A composition according to claim 12, which contains 1 to 40% by weight of organic solvent, relative to the total weight of the composition.

14. A composition according to claim 13 which contains 5 to 30% by weight of organic solvent, relative to the total weight of the composition.

15. A composition according to claim 1, which contains 0.5 to 3% by weight of thickener, relative to the total weight of the composition.

16. A composition according to claim 15 which contains 0.5 to 3% by weight of thickener, relative to the total weight of the composition.

17. A composition according to claim 1, which contains at least one antioxidant which is sodium sulphite, thioglycolic acid, sodium bisulphite, ascorbic acid or hydroquinone.

18. A composition according to claim 17, which contains 0.05 to 1.5% by weight of antioxidant relative to the total weight of the composition.

19. Process for coloring human hair which comprises mixing a composition as defined in claim 1 at the time of use with a sufficient amount of an oxidizing agent selected from the group consisting of hydrogen peroxide, urea peroxide and ammonium persulfate, allowing the mixture to act on the hair for 10 to 45 minutes and at a temperature from ambient temperature to 45° C., rinsing the hair and drying the hair.

20. A composition suitable for dyeing human hair in the presence of at least one oxidizing agent selected from the group consisting of hydrogen peroxide, urea peroxide and ammonium persulfate comprising an aqueous solution of an effective amount of an oxidation base selected from the group consisting of (a) a paraphenylenediamine, (b) 2,5-diaminopyridine and (c) a para-aminophenol and 0.005 to 2.5 percent by weight based on the total weight of the composition of, as a coupling agent, at least one of a member selected from the group consisting of 2,4-diamino n-butyl benzene, 2,4-diamino n-propyl benzene, 2,4-diamino isopropyl benzene, and a salt thereof, said composition having a pH ranging from 8 to 11.5.

21. The composition of claim 20 which also includes an effective amount of another coupling agent selected from the group consisting of resorcinol, 2-methylresorcinol, meta-aminophenol, 2-methyl-5-N-(β-hydroxyethyl)-aminophenol, 2-methyl-5-aminophenol, 6-hydroxy-benzomorpholine and 1-phenyl-3-methyl pyrazol-5-one.

22. The composition of claim 20 which also contains an effective amount of a direct dye selected from the group consisting of 3-nitro-6-N-(β-hydroxyethyl) amino anisole, 3-nitro-4-aminophenol, 3-nitro-4-N-(β-hydroxyethyl) aminophenol, 2-amino-3-nitro isopropyl benzene, 3-nitro-4-N-methylamino-N,N-di-(β-hydroxyethyl) aniline, 2-nitro-4-methyl-6-amino phenol and 2-methyl-4-amino-5-nitrophenol.

23. The composition of claim 20 which also contains from 0.5 to 55 percent by weight of a water-soluble surface-active agent based on the total weight of said composition.

24. The composition of claim 23 wherein said surface-active agent is present in an amount of 4 to 40 percent by weight of said composition.

25. The composition of claim 20 which also includes 1 to 40 percent by weight of an organic solvent to assist in solubilizing the components of said composition, said organic solvent being ethanol, 2-butoxyethanol or propylene glycol.

26. The composition of claim 25 wherein said organic solvent is present in an amount of 5 to 30 percent by weight of said composition.

27. The composition of claim 20 which also includes from 0.5 to 5 percent by weight of a thickening agent based on the total weight of said composition.

28. The composition of claim 27 wherein said thickening agent is present in an amount of 0.5 to 3 percent by weight of said composition.

29. The composition of claim 20 which also contains 0.05 to 1.5 percent by weight of an antioxidant.

30. The composition of claim 29 wherein said antioxidant is selected from the group consisting of thioglycollic acid, sodium bisulfite and hydroquinone.

31. The composition of claim 20 which includes at least one of ortho-aminophenol and pyrocatechol.

32. The composition of claim 20 wherein said oxidation base is (a) a paraphenylenediamine selected from the group consisting of paraphenylenediamine, paratoluylenediamine, 2,6-dimethyl paraphenylenediamine, N-(β-methoxyethyl) paraphenylenediamine, N,N-di-(β-hydroxyethyl)paraphenylenediamine, N-ethyl-N-(β-hydroxyethyl)paraphenylenediamine, 2,6-dimethyl-3-methoxy paraphenylenediamine, 2,5-diaminoisopropyl benzene and 2,5-diaminophenyl ethanol.

33. The composition of claim 20 wherein said oxidation base is (c) para-aminophenol selected from the group consisting of para-aminophenol and 2-methyl-4-aminophenol.

34. The composition of claim 20 wherein said oxidation base is 2,5-diaminopyridine.

* * * * *